United States Patent
Marquez et al.

(10) Patent No.: US 8,686,729 B2
(45) Date of Patent: Apr. 1, 2014

(54) NMR REACTION MONITORING FLOW CELL

(75) Inventors: Brian Marquez, Preston, CT (US); Michael Fey, Andover, MA (US); Kimberly L. Colson, Westford, MA (US); Robert Krull, Wilmington, MA (US); Eckhard Bez, Littleton, MA (US); Don Piroli, Quincy, MA (US); Werner E. Maas, Boxford, MA (US)

(73) Assignee: Bruker Biospin Corporation, Billerica, MA (US)

( * ) Notice: Subject to any disclaimer, the term of this patent is extended or adjusted under 35 U.S.C. 154(b) by 427 days.

(21) Appl. No.: 13/181,105

(22) Filed: Jul. 12, 2011

(65) Prior Publication Data

US 2012/0092013 A1 Apr. 19, 2012

Related U.S. Application Data

(60) Provisional application No. 61/363,481, filed on Jul. 12, 2010.

(51) Int. Cl.
*G01V 3/00* (2006.01)

(52) U.S. Cl.
USPC .......................................... 324/321; 324/318

(58) Field of Classification Search
USPC ................. 324/321, 322, 318, 306, 307, 300
See application file for complete search history.

(56) References Cited

U.S. PATENT DOCUMENTS

| | | | | |
|---|---|---|---|---|
| 5,247,256 A | * | 9/1993 | Marek | 324/321 |
| 5,469,061 A | * | 11/1995 | Linehan et al. | 324/321 |
| 6,486,672 B1 | * | 11/2002 | Wand et al. | 324/321 |
| 6,838,880 B2 | * | 1/2005 | Hofmann et al. | 324/318 |
| 7,728,593 B2 | * | 6/2010 | Norell | 324/321 |
| 2007/0148054 A1 | | 6/2007 | Takahashi | |

FOREIGN PATENT DOCUMENTS

| | | |
|---|---|---|
| JP | 2001208819 A | 8/2001 |
| JP | 2002107437 A | 10/2002 |
| JP | 2003139831 A | 5/2003 |

* cited by examiner

*Primary Examiner* — Louis Arana
(74) *Attorney, Agent, or Firm* — O'Shea Getz P.C.

(57) ABSTRACT

A monitoring cell, used to perform a measurement in an NMR spectrometer of a reaction fluid produced by a reaction vessel, has a body having inlet and outlet transport coaxial capillaries for transporting the reaction fluid between the body and the reaction vessel. Cooling lines are also positioned coaxially with the transport capillaries to transport cooling liquid between the body and the reaction vessel. The cell further has a hollow sample probe for insertion into the NMR spectrometer and a coupler section that removably connects the sample probe to the body so that the inlet transport capillary extends through the body into the interior of the sample probe and the outlet transport capillary is sealed to the sample probe to allow reaction fluid that enters the sample probe via the inlet transport capillary to exit the sample probe via the outlet transport capillary.

18 Claims, 3 Drawing Sheets

US 8,686,729 B2

NMR REACTION MONITORING FLOW CELL

BACKGROUND

Nuclear magnetic resonance (NMR) is a physical phenomenon involving quantum mechanical magnetic properties of atomic nuclei in the presence of an applied, external magnetic field. NMR phenomena can be observed with an NMR spectrometer and used to study molecular physics, crystalline and non-crystalline materials in a process called NMR spectroscopy.

To perform a static nuclear magnetic resonance experiment, a liquid or solid sample is typically placed in a glass tube that can be inserted into the bore of a magnet. In addition to static measurements, NMR spectroscopy can also be used to measure kinetic chemical reactions using stopped flow or continuous flow methods. In these methods, a reaction takes place in a reaction vessel that is external to the magnetic field and the reactants and products from the reaction are pumped through a continuous flow, or flowthrough, cell located in the magnetic field. This cell includes the glass tube and a structure that mimics the rotor structure used in static studies, but includes inlet and outlet transport capillary tubes in order to introduce the materials from the reaction vessel into the cell and return the materials to the reaction vessel after the measurement has been made.

Most applications of flow NMR use flow probes that are dedicated to measurements of single nucleus or group of nuclei in order to optimize the sample volume, sensitivity and resolution. Accordingly, these dedicated probes are expensive, relatively inflexible and generally have a limited temperature range.

SUMMARY

In accordance with the principles of the invention, an NMR flow cell has a flexible arrangement that allows the flow cell as well as the transport capillaries to be easily adapted to a particular reaction experiment. The cell has a body connected to an input transport capillary and to an output transport capillary that conduct the reaction fluid to be measured between the body and the reaction vessel. The cell also has a special hollow sample probe having an outer shape and size that mimics a conventional NMR sample probe and allows the sample probe to be inserted into the NMR spectrometer. The sample probe can be slid over the inlet transport capillary, which extends through the body, and removably connected to the body so that the outlet transport capillary is sealed to the sample probe. This arrangement allows reaction fluid that enters the sample probe via the inlet transport capillary to exit the sample probe via the outlet transport capillary. The inventive reaction monitoring flow cell offers high flow capabilities and good lineshape and is compatible with many existing NMR probes so that the NMR instrument can be easily converted between experiments that use the inventive flow cell and static NMR probes for multiuser NMR instruments.

In one embodiment, input transport capillary and the coaxial output transport capillary are enclosed by coaxial cooling liquid tubes that conduct temperature controlled liquid between the reaction vessel and the reaction monitoring flow cell for optimal temperature control of exothermic and endothermic reactions.

DETAILED DESCRIPTION

Figure 1:
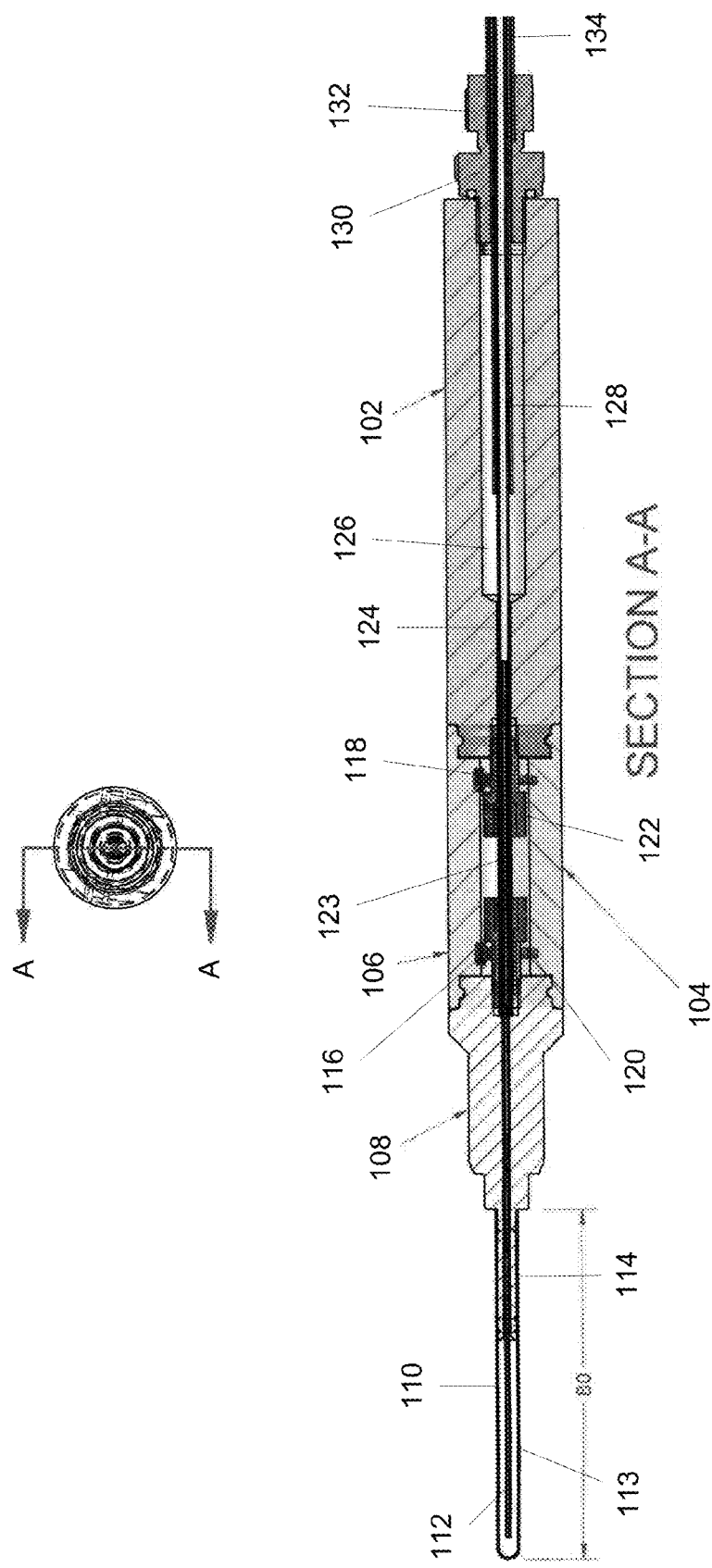
FIG. 1 is a cross sectional view of the inventive flow cell.
Figure 2:
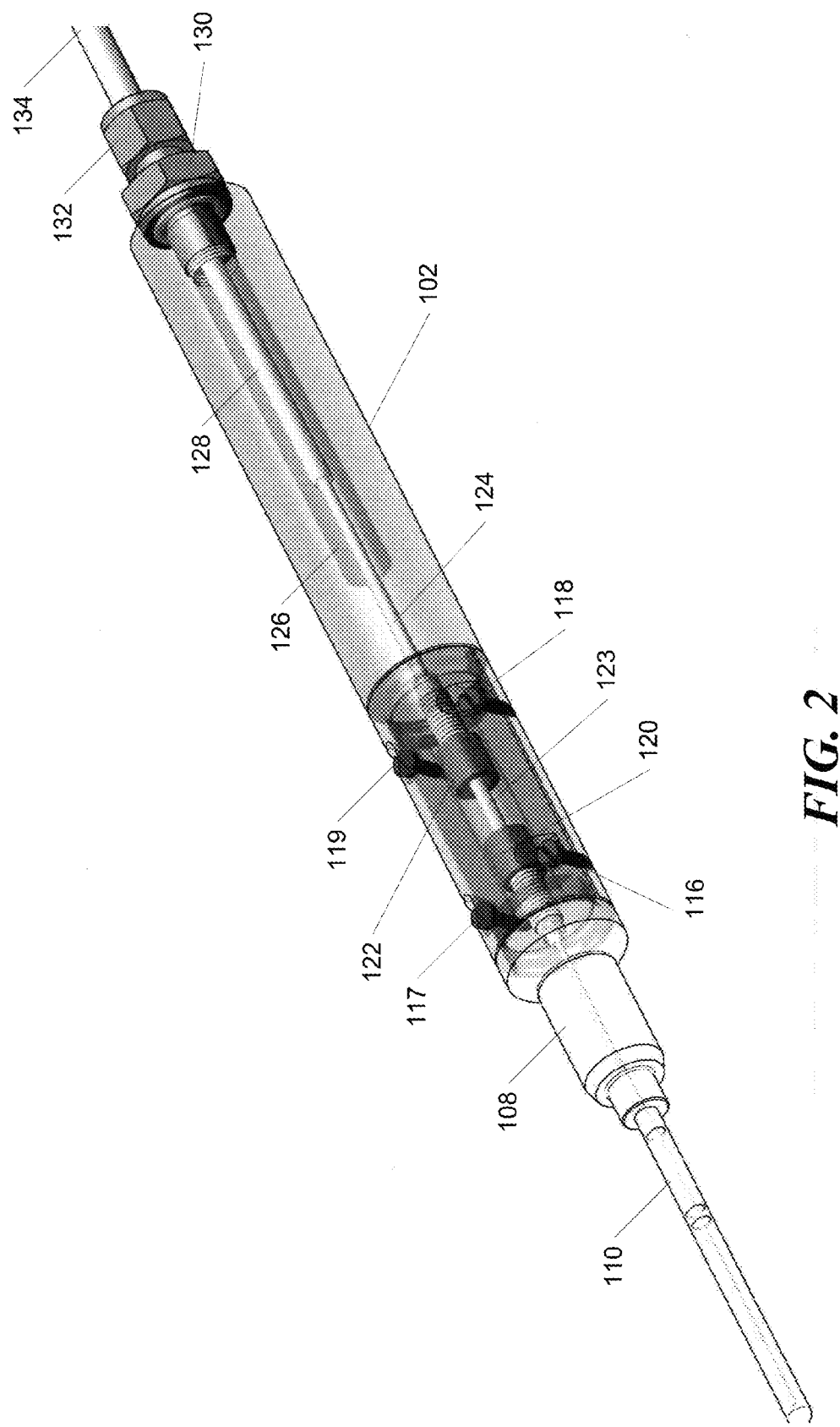
FIG. 2 is a perspective view of the inventive flow cell.

FIGS. 1 and 2 illustrate a cross sectional and perspective view of the inventive NMR flow cell. The cross section is taken along the sectional lines A-A. The cell 100 consists of four main cylindrical sections: the body 102, a coupler section 106, a ceramic head 108 and a sample cell 110. The sample cell 110 is typically formed from glass and slides over a projection 114 of the ceramic head 108 formed of a conventional ceramic material. The sample cell 110 and the ceramic head together form a probe with a shape that matches the shape of a conventional probe and rotor so that they fit into the NMR spectrometer.

The ceramic head 108 is attached to the body 102 by a coupling comprising two halves 104 and 106 which are held together with four screws 116, 117, 118 and 119. The coupling halves 104 and 106 can be formed of a polycarbonate material, such as Lexan®. The removable coupling allows the probe section (110, 108) to be easily detached from the body 102 so that the probe can be replaced without replacing the body, which is typically connected to coaxial cooling liquid lines (not shown in FIGS. 1 and 2).

The body 102 is formed of a PCTFE material, such as KEL-F and is connected to the inlet and outlet transport capillaries via fittings 130 and 132. The inlet and outlet capillaries and the inlet and outlet cooling lines are all coaxial and form a four channel coaxial structure. The inlet transport capillary 112 is the innermost channel in the four channel structure and is connected to the reaction vessel (not shown in FIGS. 1 and 2). The inlet transport capillary passes though the entire reaction monitoring cell 100 and terminates in the sample tube 110.

Reaction fluid passing through the inlet transport capillary 112 exits the end of the capillary 112 and returns via the space 113 between the outer wall of capillary 112 and the inner wall of sample tube 110. The ceramic head section 108 through which the inlet capillary 112 passes does not fit tightly around the inner capillary so that reaction fluid in the space 113 can pass between the inlet capillary 112 and the inner bore through the ceramic head 108. This fluid enters the outlet coaxial shell 123, 124 which is fastened to the ceramic head 108 via ferrules 120 and 122. Ferrules 120 and 122 are fixtures that are conventionally used in liquid chromatography columns to fasten sections together. Once the reaction fluid is inside the coaxial shell 124 it passes through the body 102 and out of the reaction monitoring cell 100.

Cooling liquid enters the cell 100 via the third chamber of the coaxial structure which is formed by coaxial shell 128. This cooling liquid enters chamber 126 in cell body 102. The cooling liquid returns via passage 126 and passes through a space between the inner wall of fitting 130 and the outer wall of shell 128. Once the cooling liquid has passes through fitting 130 it passes into the outermost shell 134 of the four channel coaxial structure and returns to the cooling apparatus (not shown in FIGS. 1 and 2).

Figure 3:
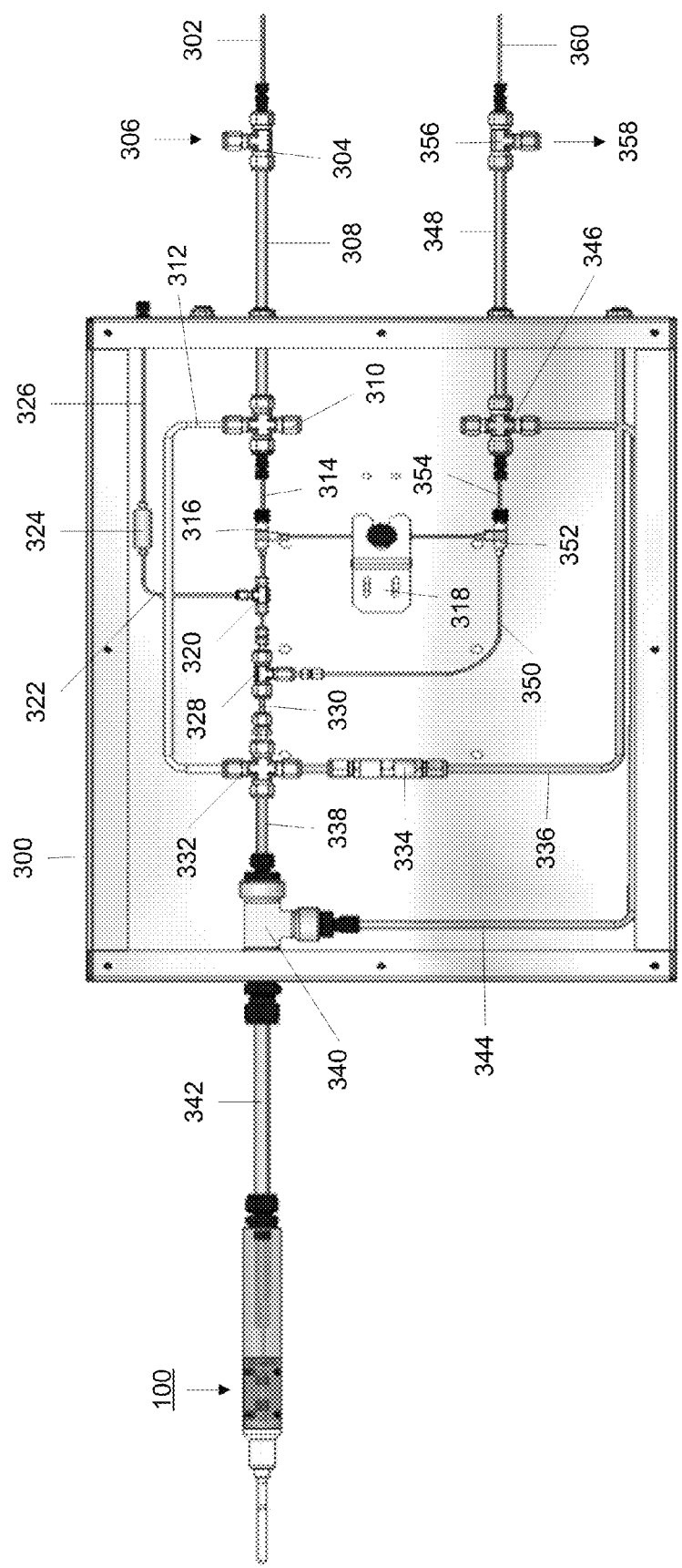
FIG. 3 is a plan view of a junction control box that allows a portion of the flow to be bypassed and also provides for over-pressure relief.

FIG. 3 illustrates a junction box 300 which connected the reaction monitoring cell 100 illustrated in FIGS. 1 and 2 to the inlet and outlet transport capillaries (302, 358) and the inlet and outlet cooling lines (306, 358). Reaction fluid in the inlet capillary 302 passes into T fitting 304 which receives cooling fluid via the cooling inlet line 306. Fitting 304 as a coaxial output 308 with the inlet reaction fluid surrounded by the cooling liquid. The coaxial line 308 passes into cross fitting 310 which strips off the cooling fluid and routes it via line 312 to cross fitting 332 while inlet reaction fluid in the inlet capillary passes through fitting 310 into line 314.

Reaction fluid in the inlet capillary 314 passes into T fitting 316 which can divert part of the fluid to bypass valve 318. Bypass valve 318 can divert part of the inlet fluid via T fitting 352 to the outlet fluid return capillary and allows the flow rate of the fluid in the cell 100 to be adjusted.

Inlet fluid passing through fitting 316 passes into T fitting 320 which is connected to overpressure relief valve 324. An overpressure situation in the inlet line causes relief valve 324 to release part of the fluid to the overflow line 326.

Inlet fluid passing through fitting 320 passes into T fitting 328 which adds another coaxial shell for outlet reaction fluid to form a two channel coaxial structure 330. The two channel structure 330 passes into cross fitting 332 which adds an additional outer shell for the inlet cooling liquid which arrives via line 312. Cross fitting 332 is also connected to overpressure valve 334, which in the case of an overpressure situation in the cooling liquid diverts some of the cooling liquid to the discharge line 336.

The three channel coaxial structure 338 containing the inlet reaction fluid in the innermost channel, the outlet reaction fluid in the next outer channel and the inlet cooling fluid in the outermost channel passes to T fitting 340 which adds the outmost shell to the coaxial structure to hold the outlet cooling liquid. The four channel coaxial structure 342 then passes to the reaction cell as previously described.

Cooling liquid returning from the cell 100 in the outermost channel of the coaxial structure is shunted by fitting 340 into line 344 to cross fitting 346. Outlet reaction fluid passes through fitting 332 to fitting 328 where it is diverted to line 350.

Outlet reaction fluid in line 350 is combined with any fluid diverted by bypass valve 318 in T fitting 352 to form the outlet line 354 which passes into cross fitting 346. In fitting 346 the outlet reaction fluid is surrounded by the outlet cooling liquid to form a two chamber coaxial structure 348. In T fitting 365, the cooling liquid is shunted to cooling liquid outlet 358 whereas the outlet reaction fluid continues through fitting 356 to the outlet reaction fluid transport capillary line 360.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. A monitoring cell for performing a measurement in an NMR spectrometer of a reaction fluid produced by a reaction vessel, the monitoring cell comprising:
    a body having an inlet transport capillary for receiving the reaction fluid from the reaction vessel and an outlet transport capillary positioned coaxially around the inlet transport capillary for returning the reaction fluid to the reaction vessel, the body receiving cooling liquid from the reaction vessel and passing the cooling liquid around the inlet and outlet transport capillaries;
    a hollow sample probe having an outer shape and size that allows the sample probe to be inserted into the NMR spectrometer;
    a coupler section that removably connects the sample probe to the body so that the inlet transport capillary extends through the body into the interior of the sample probe and the outlet transport capillary is sealed to the sample probe to allow reaction fluid that enters the sample probe via the inlet transport capillary to exit the sample probe via the outlet transport capillary.

2. The monitoring cell of claim 1 wherein the outlet transport capillary extends through the coupler section coaxial with the inlet transport capillary and is sealed to the sample probe by an elastomeric ferrule.

3. The monitoring cell of claim 2 wherein the ferrule is located in the coupler section and fits tightly to the outside of the outlet transport capillary and the inside of a recess in the sample probe.

4. The monitoring cell of claim 2 wherein a second ferrule located in the coupler section seals the outlet transport capillary to the body.

5. The monitoring cell of claim 1 wherein the sample probe comprises a tubular sample cell and a conical head.

6. The monitoring cell of claim 5 wherein the coupler section comprises a clamp that engages the head and the body.

7. The monitoring cell of claim 5 wherein the sample cell is fabricated from glass.

8. The monitoring cell of claim 5 wherein the head is fabricated from ceramic.

9. The monitoring cell of claim 8 wherein the head has a cylindrical finger that extends into the sample cell.

10. The monitoring cell of claim 1 wherein the body comprises a cavity through which the inlet transport capillary and the outlet transport capillary pass, the cavity being connected to a cooling liquid input tube for receiving cooling liquid from the reaction vessel and being connected to a cooling liquid output tube for returning cooling liquid to the reaction vessel.

11. The monitoring cell of claim 10 wherein the cooling liquid output tube coaxially surrounds the cooling liquid input tube and the cooling liquid input tube coaxially surrounds the outlet transport capillary between the reaction vessel and the body.

12. The monitoring cell of claim 10 wherein the cavity coaxially surrounds the cooling liquid input tube and the cooling liquid output tube.

13. A monitoring cell for performing a measurement in an NMR spectrometer of a reaction fluid produced by a reaction vessel, the monitoring cell comprising:
    a cylindrical body having a cavity therein;
    an inlet transport capillary connected to the body for transporting the reaction fluid from the reaction vessel to the body, the inlet transport capillary extending through the body;
    an outlet transport capillary positioned coaxially around the inlet transport capillary and connected to the body for returning the reaction fluid from the body to the reaction vessel, the outlet transport capillary extending through the body;
    a cooling liquid input tube positioned coaxially around the outlet transport capillary and connected to the body cavity for transporting cooling liquid from the reaction vessel to the body;
    a cooling liquid output tube positioned coaxially around the cooling liquid input tube and connected to the body cavity for transporting cooling liquid from the body to the reaction vessel;
    a cylindrically symmetrical hollow sample probe having an outer shape and size that allows the sample probe to be inserted into the NMR spectrometer; and
    a cylindrical coupler section that removably connects the sample probe to the body so that the inlet transport capillary extends through the body into the interior of the sample probe and the outlet transport capillary is sealed to the sample probe to allow reaction fluid that enters the sample probe via the inlet transport capillary to exit the sample probe via the outlet transport capillary.

14. The monitoring cell of claim 13 wherein the coupler section comprises a clamp that engages the head and the body.

15. The monitoring cell of claim 13 wherein the sample probe comprises a tubular sample cell and a conical head.

16. The monitoring cell of claim 15 wherein the sample cell is fabricated from glass.

17. The monitoring cell of claim 15 wherein the head is fabricated from ceramic.

18. The monitoring cell of claim 15 wherein the head has a cylindrical finger that extends into the sample cell.

* * * * *